United States Patent
Neilan et al.

(10) Patent No.: US 10,772,994 B2
(45) Date of Patent: Sep. 15, 2020

(54) COATED MEDICAL DEVICE AND METHOD OF COATING SUCH A DEVICE

(71) Applicant: COOK MEDICAL TECHNOLOGIES LLC, Bloomington, IN (US)

(72) Inventors: John Neilan, Gort (IE); David Murray, Limerick (IE); James Butler, Aherlow (IE)

(73) Assignee: Cook Medical Technologies LLC, Bloomington, IN (US)

( * ) Notice: Subject to any disclaimer, the term of this patent is extended or adjusted under 35 U.S.C. 154(b) by 220 days.

(21) Appl. No.: 15/398,184

(22) Filed: Jan. 4, 2017

(65) Prior Publication Data
US 2017/0203011 A1  Jul. 20, 2017

(30) Foreign Application Priority Data

Jan. 15, 2016 (GB) .................................. 1600808.8

(51) Int. Cl.
| | | |
|---|---|---|
| A61L 31/08 | (2006.01) |
| A61L 31/16 | (2006.01) |
| A61L 29/16 | (2006.01) |
| A61L 29/04 | (2006.01) |
| A61L 31/02 | (2006.01) |

(52) U.S. Cl.
CPC .............. *A61L 31/08* (2013.01); *A61L 29/04* (2013.01); *A61L 29/16* (2013.01); *A61L 31/022* (2013.01); *A61L 31/16* (2013.01); *A61L 2300/416* (2013.01); *A61L 2420/02* (2013.01); *A61L 2420/06* (2013.01)

(58) Field of Classification Search
None
See application file for complete search history.

(56) References Cited

U.S. PATENT DOCUMENTS

| | | |
|---|---|---|
| 6,632,470 B2 | 10/2003 | Morra et al. |
| 7,105,199 B2 | 9/2006 | Blinn et al. |
| 7,396,582 B2 | 7/2008 | Claude et al. |
| 7,597,924 B2 | 10/2009 | Kondyurin et al. |
| 8,123,799 B1 | 2/2012 | Malik et al. |
| 9,005,960 B2 | 4/2015 | Legeay et al. |
| 2003/0113478 A1 | 6/2003 | Dang et al. |
| 2006/0171980 A1 | 8/2006 | Helmus et al. |
| 2006/0194008 A1* | 8/2006 | Schwartz ................. A61L 27/32 428/34.4 |
| 2007/0225823 A1 | 9/2007 | Hawkins et al. |
| 2007/0255206 A1 | 11/2007 | Reneker et al. |
| 2008/0166470 A1* | 7/2008 | Schwartz ............... B05D 1/185 427/2.27 |
| 2009/0171453 A1 | 7/2009 | Adams et al. |
| 2009/0294732 A1 | 12/2009 | Atanasoska et al. |
| 2011/0217351 A1* | 9/2011 | Cheng ........................ A61F 2/02 424/423 |
| 2012/0290070 A1* | 11/2012 | Wang ...................... A61L 31/06 623/1.15 |
| 2013/0289702 A1 | 10/2013 | Coghlan et al. |
| 2014/0342954 A1 | 11/2014 | Ingber et al. |

FOREIGN PATENT DOCUMENTS

| | | | |
|---|---|---|---|
| EP | 0819446 | 1/1998 | |
| EP | 0819446 A2 * | 1/1998 | ......... A61K 51/1282 |
| JP | 2002-331028 | 11/2002 | |
| WO | WO2008/057568 | 5/2008 | |
| WO | WO2010/111583 | 9/2010 | |
| WO | WO 2013/152713 A1 | 10/2013 | |

OTHER PUBLICATIONS

Extended Search Report in corresponding European Application No. 17150320.4, dated Jun. 13, 2017, 7 pages.
Combined search and examination report for GB1600808.8 dated Jul. 18, 2016, 5 pgs.
Reply to combined search and examination report for GB1600808.8 dated Aug. 15, 2016, 17 pgs.
Taek Gyoung Kim et al., "Controlled Release of Paclitaxel from Heparinized Metal Stent Fabricated by Layer-by-Layer Assembly of Polylysine and Hyaluronic Acid-g-Poly(lactic-co-glycolic acid) Micelles Encapsulating Paclitaxel", Bio macromolecules, vol. 10, No. 6, Jun. 8, 2009 (Jun. 8, 2009), pp. 1532-1539.
Examination Report for EP17150320.4 dated Jul. 23, 2018, 7 pgs.
Summary of Consult with Examiner for EP17150320.4 dated Aug. 28, 2018, 5 pgs.
Examination Report for EP18168827.6 dated Oct. 19, 2018, 6 pgs.

* cited by examiner

*Primary Examiner* — Susan T Tran
(74) *Attorney, Agent, or Firm* — Brinks Gilson & Lione (57) ABSTRACT

A medical device such as a stent (10) or medical balloon (40) is functionalised prior to coating with a bioactive material (54), specifically by acidification or basification of the contact surface or surfaces (50) of the medical device. Functionalisation with subsequent coating of bioactive agent directly onto the functionalised surface provides a significantly more consistent and reliable coating of bioactive agent on a medical device without requiring containment or time release devices.

17 Claims, 9 Drawing Sheets
(3 of 9 Drawing Sheet(s) Filed in Color)

COATED MEDICAL DEVICE AND METHOD OF COATING SUCH A DEVICE

RELATED APPLICATIONS

This application claims priority to GB application no. GB 1600808.8, filed Jan. 15, 2016, titled "COATED MEDICAL DEVICE AND METHOD OF COATING SUCH A DEVICE," the contents of which applications are incorporated herein by reference.

TECHNICAL

The present invention relates to a coated medical device, particularly coated with a bioactive material, and to a method of preparing and coating such a device. The invention can be used with implantable medical devices such as stents, stent grafts, vascular filters and plugs, valvuloplasty devices and so on. It can also be applied to medical devices intended to be deployed temporarily in a patient, such as angioplasty balloons, valvuloplasty balloons, medical device deployment balloons and the like.

BACKGROUND

Coated medical devices, particularly endoluminally deployable medical devices, are known for a variety of medical applications. In the case of an implantable medical device, that is a device intended to be left in the patient permanently or over long periods of time, the device may coated with one or more layers of drugs intended for long term drug administration to diseased tissue. Treatment of cancers is an example. In other examples, the coating is provided in order to treat adverse body reactions caused by the medical treatment or by long term presence of a foreign object in the body, such as initial reactive hyperplasia, inflammation, thrombosis, restenosis and so on. In these cases the medical device is deployed only temporarily in a patient.

It is important that a bioactive coating on a medical device is consistent over the surface or surfaces of the device, is reliably formed from one device to another, is sufficiently well held on the device during deployment, and can be administered into the patient at the desired rate once the device is deployed. For instance, a coating on an implantable device such as a stent, filter, vascular plug or the like may need to be released over an extended period of time such as weeks, months or years, whereas a coating on a medical balloon, such as an angioplasty balloon or a device delivery balloon, may need to be released over a period of seconds or minutes.

Applying a bioactive agent to an untreated surface of a medical device often fails to form a uniform or reliable coating, leading to variable bioactive results. This is particularly the case with lipophilic materials including, for instance, paclitaxel, which has been proven to be a very effective anti-restenosis drug.

Attempts have been made in the art to treat one or more surfaces of medical devices to improve their biocompatibility and also to seek to improve the adherence of one or more coatings onto the medical device. These known treatments, however, have failed to provide consistent, reliable and repeatable surface characteristics for many bioactive agents. Failure to provide an adequate coating can result in failure to meet the strict drug release required by the FDA USP pharmacopeia drug device requirements and that of other regulatory bodies.

Other attempts in the art have involved providing for containment of the bioactive agent, for instance in a containment device such as a polymer matrix, by applying an outer layer or coat over the layer of bioactive material, by encapsulating the bioactive agent in capsules or other carriers, and so on. Such containment mechanisms, which restrain the bioactive material on the device and control the release of the material into the patient, can often cause other clinical issues, including reduction in the amount of bioactive material which can be carried on the medical device and inadequate release rate of the bioactive material. Furthermore, the containment device can act as a target for long term restenosis and other foreign body reactions. Despite such drawbacks, containment devices are still often proposed in order to seek to overcome the difficulty of adequately holding the bioactive material to the medical device and of ensuring adequate dosage of bioactive material in order to try to meet regulatory criteria.

Some examples of known surface treatments are disclosed in U.S. Pat. Nos. 7,597,924, 7,396,582, 6,632,470, 8,123,799, 9,005,960 and US-2009/171453, the contents of which application are hereby incorporated by reference.

SUMMARY

The present invention seeks to provide an improved coated medical device and method of preparing and coating such a device.

According to an aspect of the present invention, there is provided a method of coating a medical device having a structure for implantation or disposition inside a patient, the structure including at least one surface for coating, the method including the steps of:

functionalising the at least one surface of the structure by subjecting the at least one surface to acidification by a polar acid or to basification by a polar base, to form at least one functionalised surface; and applying a material coating directly on so as to overlie the at least one functionalised surface of the medical device, the coating being or including a conjugate base component of the polar acid, or being or including a conjugate acid component of the polar base.

Preferably, the material coating is a bioactive material coating.

The inventors have discovered that a significant increase in surface energy and adhesion characteristics can be achieved by functionalising the surface of the structure with an acid or base. In practice, such functionalization creates acid or base polar species on the surface, which bind by strong covalent or Lewis bonds to the conjugate bioactive material layer. The inventors have discovered that such functionalization can lead to increases in overall surface energies of up to 60 to 75 Dynes/cm or more when measured by the OWRK method and with polar surface energies as disclosed herein. This, coupled with the polar components created on the contact surface, forms a highly reactive surface to which the (bioactive) material layer binds. More particularly, the functionalisation taught herein amplifies the polar surface energy related to the type of functionalisation while suppressing other polar components of the surface energy. As described in detail below, acidification, for example, can increase the polar acid surface energy while reducing and in some cases completely suppressing the base polar components, and vice versa. As a result, it is not necessary to restrain the (bioactive) material in any containment mechanism, such as a containment polymer, matrix or the like.

In the preferred embodiments, the at least one surface of the medical device may be functionalised by carboxylic based acidification or by citrate basification. These have proven to be particularly effective, as described in detail below.

Advantageously, the step of functionalising the at least one surface causes an increase in acidic or base polar components at the at least one surface.

As a result, the coating may consist of or be principally of bioactive material. In other words, it may be free of containment elements, binding agents, and/or of polymer or other matrix material.

It is preferred that the functionalised surface is substantially impervious to the material coating. In other words, it is preferred that the bioactive material is in the form of a distinct layer overlying the functionalised surface and preferably does not penetrate at all, or only minimally, into the functionalised surface.

Preferably, the entirety of the at least one surface is functionalised. This ensures a consistent and uniform coating of bioactive agent.

Advantageously, the coating is or includes a therapeutic substance. The coating may be or include an anti-proliferative bioactive substance, for instance paclitaxel or derivatives thereof.

In the preferred embodiment, the method includes the step of atomically cleaning the at least one surface prior to functionalisation. Such cleaning can increase the uniformity of functionalisation of the surface and the amount of bioactive material which can be reliably carried by the device.

Preferably, the at least one surface is atomically cleaned without removal of the oxide on the at least one surface. The at least one surface may be atomically cleaned by plasma cleaning, for example an $O_2H_2$ plasma. Other suitable plasmas may be used, for example of purified water or of evaporated ethanol.

The method may also include the step of cleaning the at least one surface with an alcohol prior to functionalization, in order to remove contaminants from the surface. Advantageously, the step of cleaning the at least one surface with alcohol is carried out prior to any atomic cleaning of the surface. Ethanol is a suitable cleaning agent for this step.

The acids used for functionalisation of the surface may have a range of acidities. A strong acid, of around 1.5 pH acidity, is particularly effective.

In a practical embodiment, the at least one surface may be functionalised by treatment with an acid or a base for around five minutes. Treatment times may vary, for instance in dependence upon concentration of the acid or base, strength of the acid or base and so on.

In some embodiments, the at least one surface may be functionalised by treatment with citric acid, acetic acid, lactic acid, ascorbic acid, tannic acid, adipic acid or by conjugates thereof.

It is preferred that the at least one acidic component includes one or more of:
O—C=O
C—O, C—OH and
C=O.

The at least one functionalised surface may also include a dispersal facilitator, such as a C—C component:

Advantageously, the functionalised surface is thin, for instance having a depth of around 10 nanometres. Preferably, the functionalised surface has a depth of no more than 200 nanometres. The depth of the functionalised surface may depend on the nature of the acid molecules. For instance, tannic acid molecules are large and will produce a functionalised surface which is relatively deeper, such as between 100 and 200 nanometres. On the other hand, acids with smaller acid molecules can provide thinner functionalised surfaces, for instance of no more than 100 nanometres.

The medical device may be of any of the varieties described above and elsewhere in this specification. Examples include stents and medical balloons. Where the medical device is a stent or has a similar support member or scaffold the medical device may be made of a metal or metal alloy, such as a nickel titanium alloy. The stent could equally be made of other materials known in the art.

Where the medical device is or includes a balloon, or otherwise would benefit from fast release of the bioactive material, the coating may include or overlie an excipient.

According to another aspect of the present invention, there is provided a medical device including:
a structure for implantation or disposition inside a patient, the structure including at least one surface for coating;
wherein the at least surface is functionalised by at least one polar acid or by at least one polar base component, so as to be a functionalised surface; and
a material coating disposed directly on so as to overlie the at least one functionalised surface of the medical device, the coating being a conjugate base or including a conjugate base component of the polar acid or being a conjugate acid or including a conjugate acid component of the polar base. The coating is preferably a bioactive material coating.

The at least one functionalised surface of the medical device may include one or more carboxylic acid or citrate base components. It preferably has an increased acidic polar or base polar composition compared to a remainder of the structure of the medical device.

The coating preferably consists of or is principally of bioactive material. Advantageously, coating is free of containment elements, binding agents, polymer and/or other matrix material.

It is preferred that the functionalised surface is substantially impervious to the material coating.

In the preferred embodiments, the entirety of the at least one surface is functionalised.

Other aspects and advantages of the teachings herein are described below in connection with the preferred embodiments disclosed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments of the present invention are described below, by way of example only, with reference to the accompanying drawings, in which.

DESCRIPTION OF THE PREFERRED EMBODIMENTS

It is to be understood that the drawings are schematic only and not to scale. Often only the principal components relevant to the teachings herein are shown in the drawings, for the sake of clarity.

The embodiments described below focus on a coated stent and a coated balloon. It is to be understood, however, that these are examples only and that the teachings herein can be applied to a large range of medical devices, both for temporary placement in a patient and also for long term placement. Other examples include stent grafts, vascular filters and plugs, valvuloplasty devices, prostheses and so on.

Figure 1:
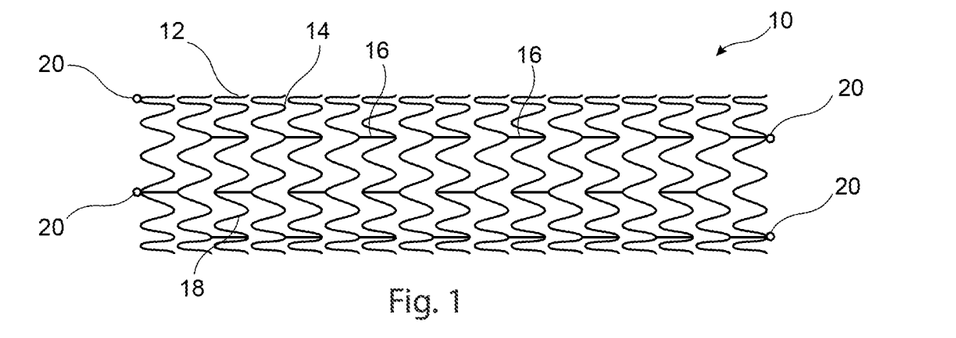
FIG. 1 is a side elevational view of an exemplary vascular stent.

Referring first to FIG. 1, there is shown an exemplary vascular stent 10 to which the teachings herein can be applied. The stent 10 is generally a tubular structure 12 in this example formed of a plurality of stent rings 14 which extend in series coaxially along the length of the tubular structure 12 and are coupled to one another by means of tie bars 16, well known in the art. In this example, the stent rings 14 are formed of a plurality of strut sections 18 arranged a zigzag shape. At the end of the stent 10 there may be provided radiopaque markers 20, again of a type well known in the art.

The stent 10 may be self-expanding or balloon expandable and made of any suitable material, of which many are known in the art.

Figure 2:
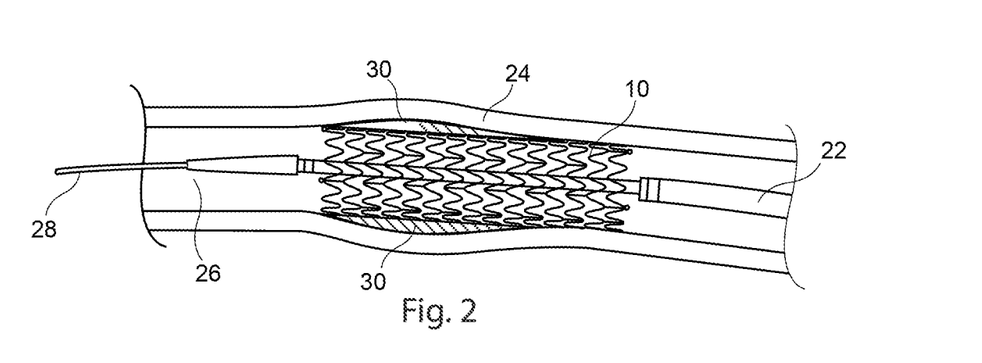
FIG. 2 is a schematic representation of the stent of FIG. 1 in the process of being deployed in a patient's vessel to treat a stenosis.

Referring also to FIG. 2, the stent 10 can be seen in the process of being deployed into a vessel 24, by means of an introducer assembly of which the distal end components 22 are visible in FIG. 2. These typically include a carrier element having a dilator tip 26 at the distal end thereof. The dilator tip 26 has a lumen therein for the passage of a guide wire 28. The components of the introducer assembly are not relevant to the teachings herein.

In the example in FIG. 2, the stent 10 is being deployed in order to treat a stenosis 30 of the vessel 24 and also to keep the vessel 24 open for the passage of blood therethrough.

Often, the deployment of a stent alone in the vessel does not provide a permanent solution as restenosis can often occur, closing the vessel again. This can be caused by a number of factors, including damage to the tissue of the vessel 24 during the vessel opening or angioplasty procedure, reoccurrence of the original causes of the stenosis, body reaction to the presence of a foreign body in the vessel, and so on Referring now to FIG. 3, this shows an exemplary medical balloon 40 which may be used for angioplasty procedures, for deployment of a medical device such as a stent or stent graft, for valvuloplasty procedures or the like. The medial balloon is fitted to a balloon catheter 42 and has a substantially cylindrical balloon body 44 terminating in end cones 46, 48 which taper towards the balloon catheter 42 and fix the balloon wall to the catheter in fluid-tight manner. The balloon catheter 42 may include a lumen therein for the passage of a guide wire 28 as well as a lumen for providing inflation fluid into the balloon. The basic structure of the balloon 40 may be of a type conventional in the art, prior to modification by the teachings herein. Although FIG. 3 depicts a simple balloon structure, it may have any of the features known for such balloons, including surface roughening, texturing and so on.

Figure 3:
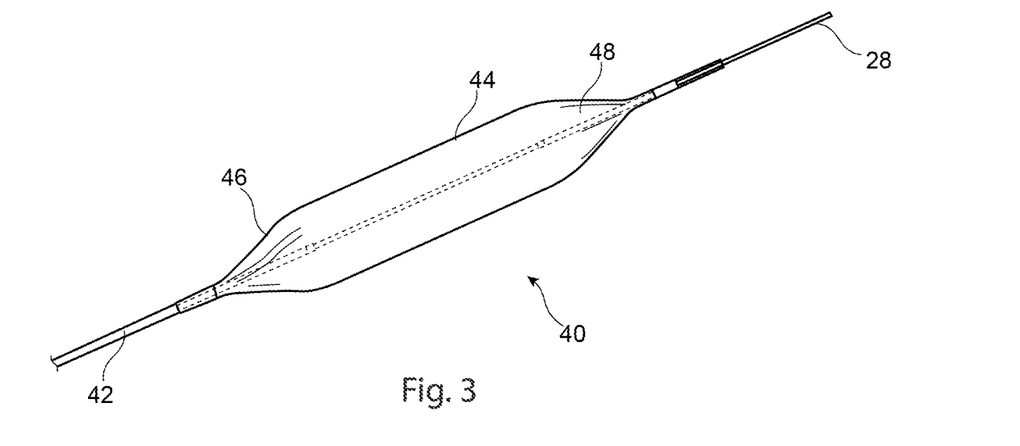
FIG. 3 is a side elevational view of an exemplary angioplasty balloon.

An angioplasty balloon of the type depicted schematically in FIG. 3 is often able to open a closed vessel in a very short period of time, for instance in seconds or minutes. Whilst the initial procedure is fast, there is the risk significant risk of further closure of the vessel, for instance by repeated collapse or restenosis. This can be caused by a number of factors including reactive hyperplasia resulting from the vessel opening procedure. Vessel closure can occur again within a few weeks or months of the medical procedure.

In the examples described briefly above in connection with FIGS. 2 and 3, it has been found that the administration of suitable bioactive agents into the vessel wall from the stent and/or from the medical balloon can substantially retard or prevent subsequent closure of the vessel due to restenosis. A variety of bioactive agents suitable for such purposes are known in the art including, for instance, antithrombogenic agents, thrombin inhibitors, tissue plasminogen activators, thrombolytic agents, fibrinolytic agents, vasospasm inhibitors, antiplatelet agents, antiproliferative agents and so on. A particularly effective bioactive agent known in the art is paclitaxel, others including dexamethasone, Sirolimus (also known as rapamycin), heparin and numerous other agents and compounds. A list of suitable bioactive agents is given at the end of this specification, though it is to be understood that the list is not exhaustive.

The bioactive material is coated onto the medical device, for example the stent 10 of FIG. 1 or the balloon 40 of FIG. 3, so as to be released from the medical device into the tissues of the vessel 24, and should be dispensed at a rate suitable for treating the required medical condition. In the case of a stent or other implantable medical device, it may be desirable for the bioactive material to be released over a prolonged period of time, for example weeks or months. In the case of a medical device which is temporarily deployed in a patient's vessel, such as angioplasty balloon or a device deployment balloon, the bioactive agent must typically be released from the balloon in a very short period of time, for instance within seconds or minutes, although sometimes could be up to an hour or more.

It is important that the bioactive agent is held onto the medical device during deployment of the device in the patient without excessive loss of bioactive material into the patient's bloodstream, for instance. For this purpose, the prior art has suggested restraining the bioactive material, for instance in a containment or time release layer or matrix. Examples include: porous polymer layers into which bioactive material can be embedded, enclosed chambers holding the bioactive material, outer coatings disposed over the bioactive material and which dissolve or open during the deployment process, encapsulation of the bioactive material in capsules or pellets, and so on. Such containment measures can lead to a number of disadvantages, including undesirable delayed administration of the bioactive material into body tissues, presence of a foreign substance in the body, possible onset of stenosis caused by the carrier device, and so on.

The optimal solution is to apply the bioactive agent in the absence of any containment or time release substance and from a layer which is predominantly or entirely made of bioactive agents. In this manner, after administration of the bioactive agent or agents, the medical device remains free of agent delivery substances (polymer layers, for example) and no unnecessary carrier substances are released into the patient's body. The problem, however, has existed with getting a bioactive agent to be held sufficiently well on the medical device.

The inventors have discovered that certain treatments of the medical device, and in particular the surface or surfaces of the device intended to be coated with one or more bioactive agents, can substantially increase the adhesion of the bioactive agent to the medical device before and during deployment of the medical device in the patient.

Specifically, as described in detail below, the inventors have discovered that functionalising the surface of the medical device to be coated by acidification or basification can substantially increase the adhesive characteristics of the surface, to such an extent that it is not necessary to use other mechanisms to retain the bioactive agent on the device. They have also discovered, as demonstrated below, that this functionalisation can allow significantly more bioactive agent to be carried on the medical device.

The term functionalisation as used herein denotes the treatment of the or one or more surfaces of the medical device with an acid or base to cause a change in the surface characteristics of the surface. The choice of acid or base functionalisation is dependent upon the nature of the bioactive material or materials which will coat the surface or surfaces. Specifically, functionalisation is by the conjugate of the nature of the bioactive material. For instance, for a bioactive material which is a base (or predominantly a base) the surface is functionalised by acidification. On the other hand, for a bioactive material which is acidic (or predominantly acidic) the surface is functionalised by basification. Functionalisation deposits onto the surface or surfaces acid or base species, which bind to the device surface and provide a bonding site for the base or acid conjugate of the bioactive material. In many cases the acid or base species are deposited as individual molecules. They do not form a polymer matrix, for instance. Bonding of the bioactive agent is by means of covalent forces, in which the base/acid or acid/base combinations form a Lewis adduct. Bioactive material molecules which overlie those directly attached to their covalent species will bind to other bioactive material molecules by same species covalent bonds.

In practice, the functionalisation leads to an increase in the polar acid or polar base component of the surface or surfaces, which leads to a significant increase in the quality of adhesion of bioactive agent to the contact surface of the medical device also to a substantial improvement in uniformity of coating across the contact surface(s) of the medical device.

The functionalisation process does not remove the oxide layer on the contact surface or surfaces, but attaches acidic or base components to the oxide layer. The attached acidic or base components could be described as becoming part of the oxide layer. Leaving the oxide intact maintains the stability of the treated surfaces of the medical device while altering the bonding properties of the oxide layer.

As will be apparent from the examples below, significant improvement in bioactive material retention is experienced by functionalisation alone. Better retention is achieved, though, by first cleaning the contact surface or surfaces of the medical device to remove impurities, generally acquired during and after the manufacturing process. This can substantially increase the amount of carbon functional groups on the contact surface(s) of the medical device, leading to an even more uniform coating of bioactive material across the contact surface of the medical device.

Functionalisation by acidification may be carried out by a relatively strong acid, for instance having a pH of around 1.5, although tests have shown that a large range of acids in a large pH range can be effective also. Functionalisation by basification may be carried out with a base of pH of around 8 to 9, although is possible with a variety of bases in a large pH range.

The examples described below relate to functionalisation by acidification. Citric acid and citrate are used as example materials for this functionalisation. It is believed that citrate acts as an acid as a result of its amphoteric properties. Other suitable carboxylic acids include acetic acid, lactic acid, adipic acid, oxalic acid, formic acid, levulinic acid and the like. Tests have also been performed using ascorbic acid and found to be advantageous. The skilled person will recognise from the teachings herein that many other acids can be used to achieve the same effects. It will be apparent that conjugates and derivatives may be equally suitable for such purposes. As an example only, hydroxamic acid is a suitable derivate of carboxylic acid.

The specific embodiments described below are directed to a stent formed of nickel titanium alloy (for instance Nitinol) which is coated with paclitaxel, a preferred bioactive agent. The skilled person will appreciate that this is an example only and that the teachings herein are applicable to the other stent materials, including metals, metal alloys and also polymer based stents. The teachings herein are not limited to stents only and can be applied to other medical devices including balloons.

Figure 4:
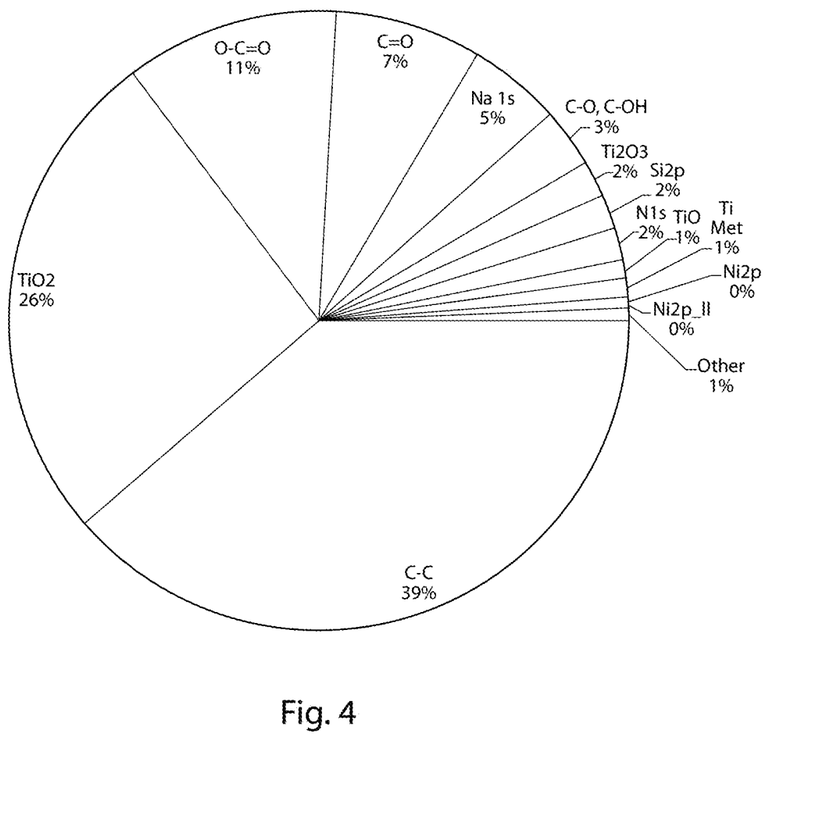
FIG. 4 is a chart depicting the constitution of a cleaned non-functionalised contact surface of a Nitinol stent.

Referring now to FIG. 4, this shows the constitution of a contact surface of a Nitinol stent, measured by x-ray photoelectron spectroscopy (XPS) following functionalisation of the surface with citric acid. As explained above, this functionalisation deposits onto the device surface acidic species which change the adhesive characteristics of the surface. As can be seen from FIG. 4, the treated contact surface exhibits a high percentage of carbon-to-carbon (C—C) components, a high proportion of titanium dioxide and also other components including O—C=O, C=O and other carbon and oxygen components.

Functionalisation by acidification substantially reduces the amount of nickel at the contact surface, which the inventors have discovered adversely affects the retention of bioactive agents on the contact surface.

The acidic species and the titanium dioxide on the treated contact surface increase the acidic polar component of the surface energy of the contact surface of the medical device, providing good adhesion characteristics to the surface, for holding a bioactive agent (being the conjugate base) onto the contact surface of the medical device. This is substantially better than what can be achieved with a non-functionalised contact surface of a medical device. Furthermore, this process of functionalisation by acidification increases the reliability of the coating process such that a more consistent dosage of bioactive agent is applied on the contact surface during batch coating.

Even though it has been found that functionalisation by acidification only provides a notable increase in adhesion of a bioactive agent onto the medical device, it has been found that cleansing of the contact surface or surfaces of the medical device prior to acidification results in even better bioactive material retention on the medical device. This is demonstrated below in connection with FIG. 7.

Figure 5:
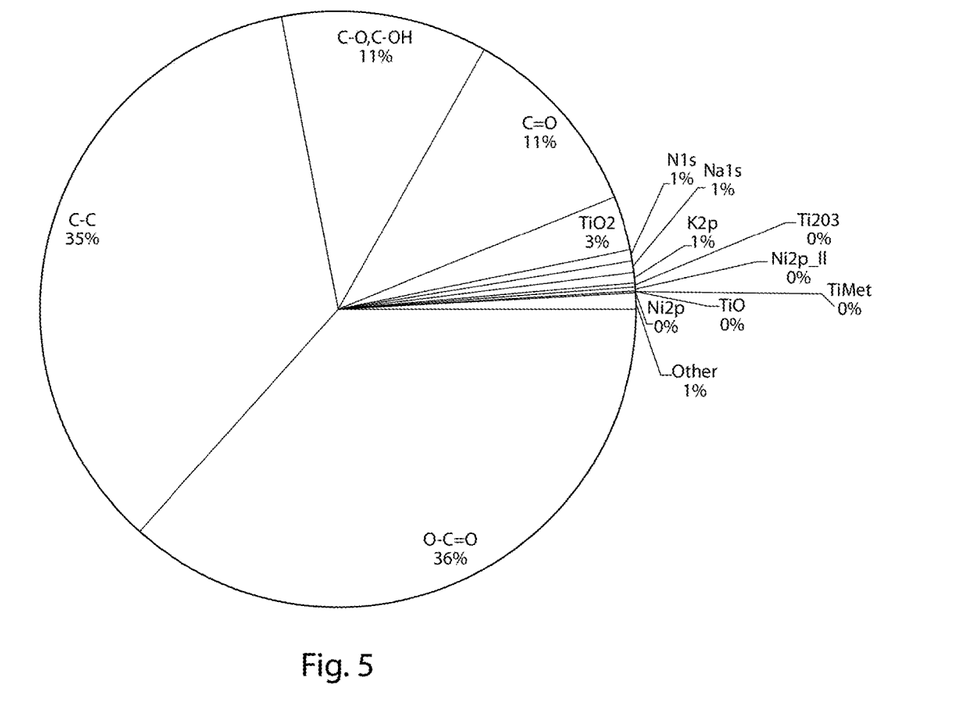
FIG. 5 is a chart depicting the constitution of a functionalised contact surface of a Nitinol stent according to the teachings herein.

Referring first to FIG. 5, this shows the constitution of a contact surface of a Nitinol stent which has been ethanol cleaned then atomically cleaned, for example by means of a plasma, and then acidified, in this example by use of citric acid.

Cleaning with an alcohol such as ethanol, can remove larger impurities from the contact surface. Plasma cleaning provides an atomically cleaned surface, removing in particular carbon components which may have adhered to the contact surface during or after manufacture. The plasma treatment is chosen to be relatively low energy so as not to remove the oxide layer on the outer surface(s) of the medical device.

Suitable plasma machines include the Gatan Solarus Model 950 and Diener Femto type B. An example of an appropriate plasma cleaning treatment, for an $H_2O_2$ plasma, has the following characteristics:

Vacuum=509-531 mTorr
Turbo Pump=750 Hz, 1.0 A
$H_2$ flow=6.3-6.4 sccm
$O_2$ flow=27.4-27.5 sccm
Power=50 W
Treatment time=5 minutes.

Plasma pre-treatment results in the generation of an even greater extent of functionalised carbon bond species at the contact surface of the medical device during the process of acidification, as can be seen in FIG. 5. The amount of titanium dioxide at the contact surface is substantially reduced compared to the case of functionalisation only (FIG. 4). The predominant acidic species of the contact surface are, in this example: O—C=O, C—O, C—OH and C=O. These species provide an acid polar element to the surface energy of the contact surface(s) of the medical device and one which is very stable across the entire extent of the contact surface. As a result, even better retention of the bioactive agent to the contact surface is achieved.

Figure 6:
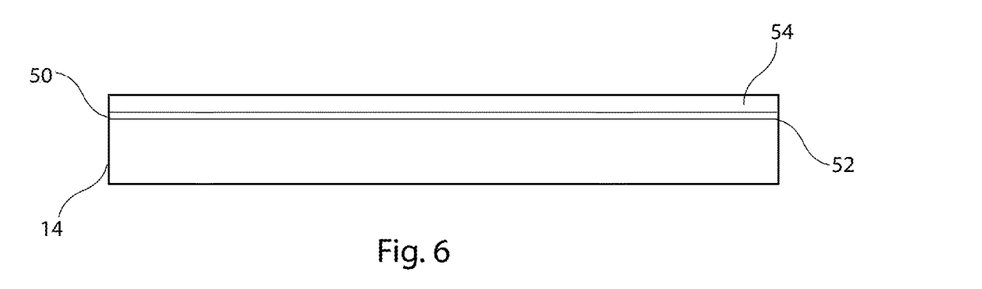
FIG. 6 is a schematic diagram of a transverse cross-sectional view of a stent strut of the stent of FIGS. 1 and 2 to show the functionalised contact surface and bioactive material coating.

Referring briefly to FIG. 6, this shows a transverse cross-sectional view of a stent, such as the stent 10 shown in FIG. 1. The tubular structure 12 of the stent, in particular strut 14, thereof has had its contact surface 50 functionalised by acidification or basification (with or without pre-cleaning) so as to have a functionalised contact surface 52 with the characteristics shown for example in FIGS. 4 and 5. Bioactive agent 54 is deposited onto the functionalised contact surface 52 (for example by spraying, rolling or dipping). It is not necessary to embed the bioactive agent in any containment matrix or layer, as is necessary with the prior art. It is preferred that the bioactive agent layer 54 is distinct from the base support (formed of the structure 14 and functionalised surface 52). Thus, the exposed surface of the bioactive material layer 54 is solely the bioactive material (and possibly any functional groups includes with it, such as excipients and so on).

Figure 7:
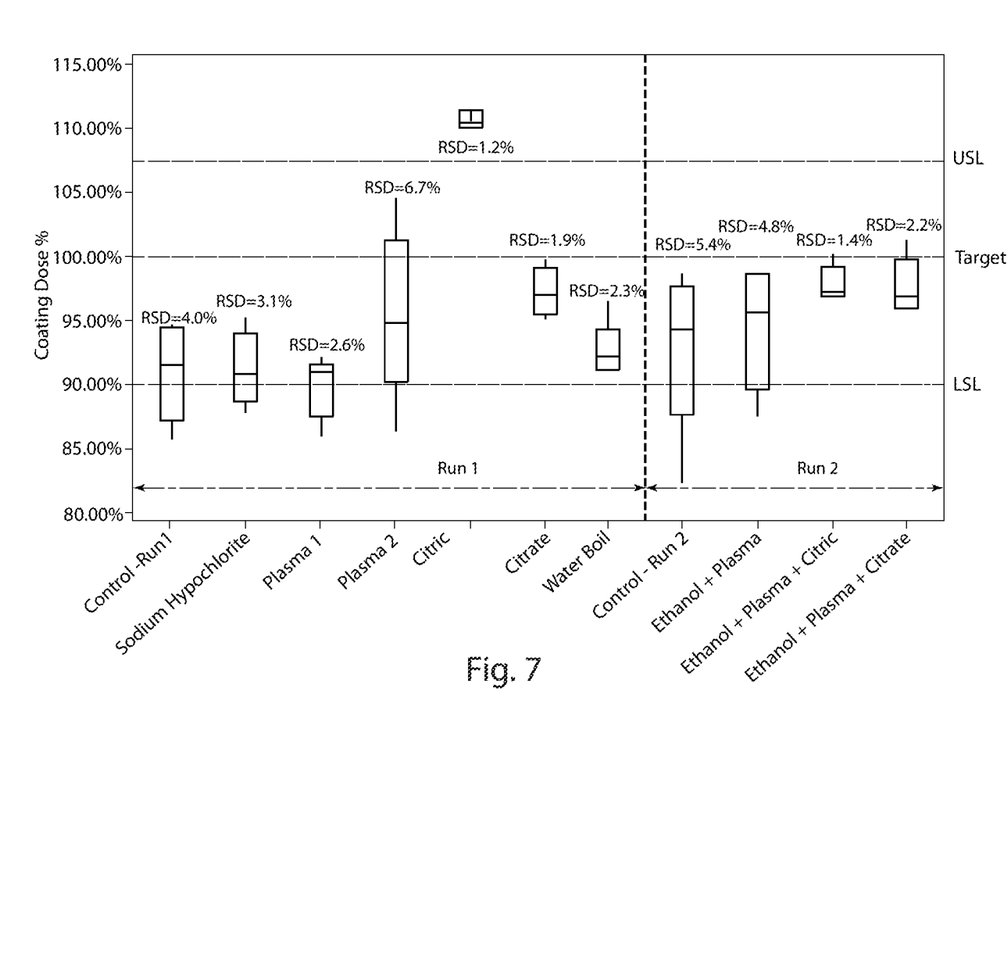
FIG. 7 is a chart showing the coating dose and spread based on different stent contact surface treatments.

Referring now to FIG. 7, this shows the effect of the functionalisation of the example stent, both by way of acidification or basification only and with pre cleaning. FIG. 7 shows percentage of coating dose relative to a desired target of 100% and what is achieved by a variety of untreated and treated stents. FIG. 7 shows the result of two different sets of experiments, indicated as "Run 1" and "Run 2" in FIG. 7. In each instance, a batch of stents was coated with bioactive material, using the same coating process and coating parameters, typically spraying with a solution of bioactive agent and drying.

Considering first Run 1, the control is an untreated stent, coated with a bioactive agent. As can be seen in FIG. 7, the maximum amount of bioactive agent on the contact surfaces was less than 95% of the target dose, with a significant spread of dosages of bioactive agent on the contact surface or a batch of untreated stents. A significant proportion of these stents had a drug dosage below the lower acceptable limit of 90%. In practice, this represents a significant proportion of medical devices not achieving the required drug dosage characteristics and not being usable.

The next three examples are of a stent cleaned with sodium hypochlorite (to reduce nickel content at the contact surface) and cleaned with two different plasmas. The first plasma (Plasma 1 in FIG. 7) is as that described above. The second example plasma (Plasma 2) is a microwave plasma with a power of 1 kW and operated for 1 minute. It has been found that Plasma 2 applied to a test sample measured a carbon reduction from 64% of the total surface to 40% after ethanol washing and by a further 16% after plasma cleaning.

As can be seen, these cleaning steps alone do not achieve any significant improvement in the amount of drug held the medical device or in the spread of the amount of drug on the device within a batch of stents. The same occurs with stents cleaned in boiling water.

In Run 1, as shown in FIG. 7, batches of stents were also coated following functionalisation with citric acid and citrate, respectively. The results with citric acid, which exhibited a coating dosage well above the target level of 100%, indicates that the bioactive material coating stage can be shortened to achieve adequate coating levels. In both instances, as can be seen, there is a substantial increase in the amount of drug attached to the medical device, together with a very substantially reduced spread of dosage levels across each batch of medical devices. This is a substantial improvement over existing methods and achieved without requiring any constraining or containment element on the medical device or provided in the layer of bioactive material.

Referring now to Run 2 shown in FIG. 7, this shows the effect of pre-cleaning of the stent prior to coating and also of pre-cleaning prior to acidification and then coating. The batch of control samples of Run 2 was similar to the control samples of Run 1, although in this example the batch exhibited a greater spread of drug dosage levels within the batch.

Cleaning with ethanol and plasma (with no functionalisation), as can be seen, results in a slight improvement in the amount of drug which attaches to the medical device and also a slight reduction in the spread of drug dosage levels across the samples of the batch. The effect of functionalising the contact surfaces of the medical device, in these examples with citric acid or citrate, exhibits a very substantial improvement both in the amount of drug held on the medical device and also in terms of the spread of dosage levels across the samples of the batch.

Figure 8:
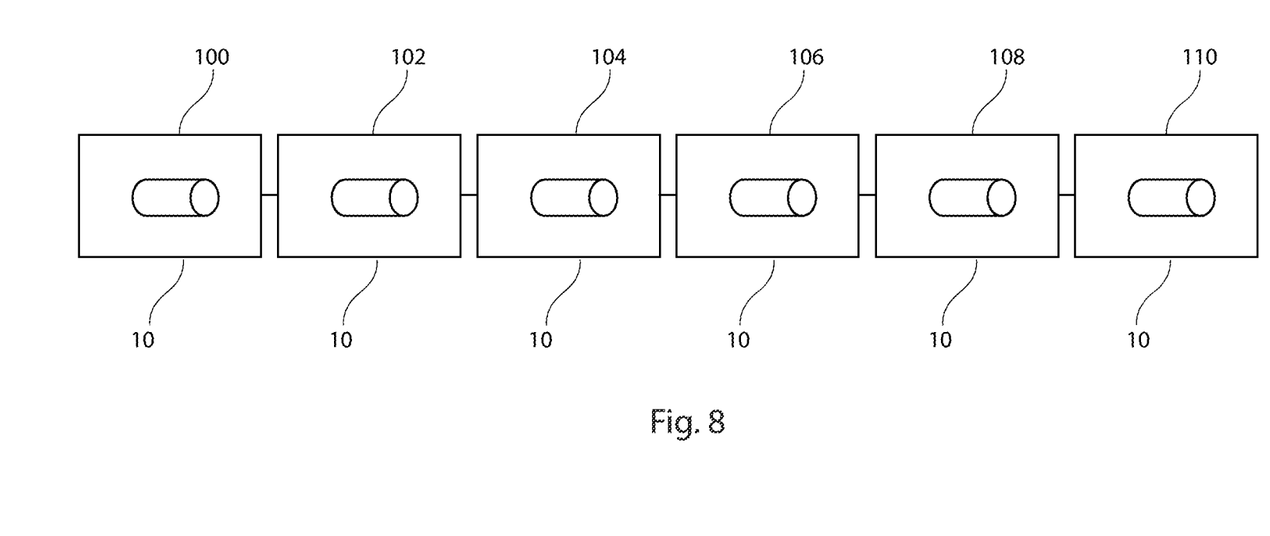
FIG. 8 is a schematic diagram of an exemplary stent preparation and coating system for practicing the teachings herein.
Figure 9:
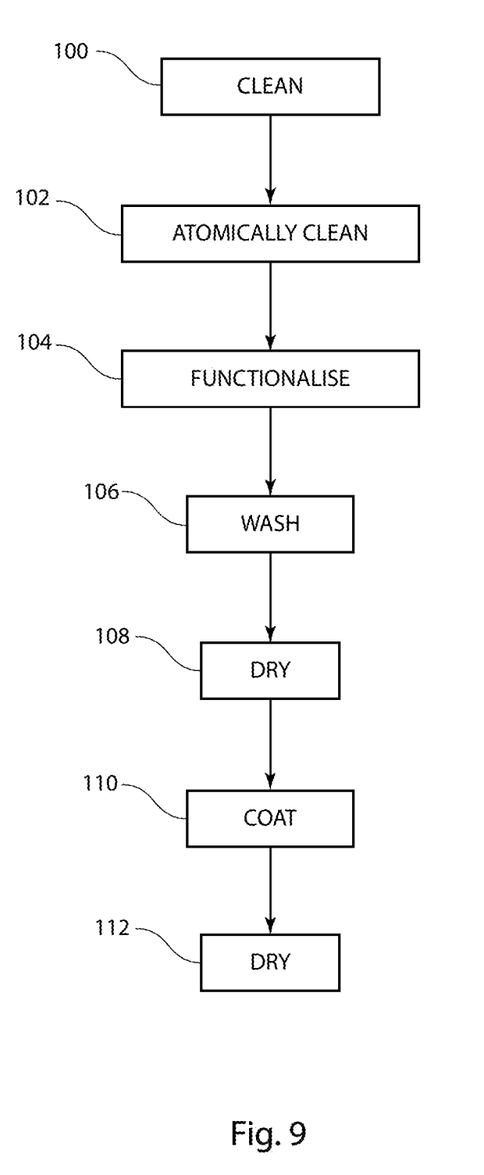
FIG. 9 is a flow chart of the preferred stent preparation and coating method.

Referring now to FIGS. 8 and 9, these show in schematic form an embodiment of system and method for functionalising and coating a medical device according to the teachings herein. The examples shown in FIGS. 8 and 9 functionalise and coat a stent. Common reference numerals are used between the system depicted in FIG. 8 and the process depicted in FIG. 9, for the sake of clarity.

An optional first cleaning stage 100 cleans the stent 10 to remove large scale impurities and this may, as explained above, be by cleaning with ethanol or other suitable alcohol. This step 100 may not be necessary in many instances.

Stage 102 provides atomic cleaning of the stent 10, preferably by a plasma, most preferably by a low energy plasma. One example is an $O_2H_2$ plasma which can remove impurities at the atomic level, whilst leaving the oxide layer on the base structure of the medical device intact. As explained above, other cleaning plasmas may be used, including for example of purified water and evaporated ethanol. Any other suitable atomic cleaning could be used in place of a plasma, for instance cleaning by $UV\text{-}O_3$, also known as UV Ozone.

Stage 104 functionalises the contact surface or surfaces of the stent 10 by applying an acid or a base to the contact surface or surfaces. This could be by dipping, rolling, spraying or any other suitable method. In one example, the stent 10 is dipped into an acid or base bath for a few seconds to a few minutes (five minutes being suitable although this could be more or less). The acid or base may be at a concentration of around 1 g per 10 ml, although this depends on the nature of the acid/base used, the time of the functionalisation stage and so on. These are parameters which a person skilled in the art will be able to determine by routine experimentation.

At stage 106, which is an optional stage, the stent 10 may be washed, for example in a solution of ethanol or other suitable solvent, in order to remove any remaining acid/base solution from the surface of the stent. At step 108, the stent is allowed to dry, prior to coating at stage 110. Coating can be by spraying, dipping, rolling or any other suitable method, typically in a solution containing the bioactive agent. The coated stent is then dried, at step 112.

The functionalised surface of the stent 10, having a high polar acid or polar base component, readily attracts its conjugate bioactive agent. This functionalisation provides a uniform and consistent coating of bioactive agent across the contact surface or surfaces of the stent and therefore a consistent dose of bioactive agent. Furthermore, as will be apparent from the above, a greater amount of bioactive agent will typically attach to the contact surface of the stent.

The higher surface energy of the stent permits a greater of variety of coating methods as less reliance on a coating method is required given the greater adhesive characteristics of the functionalised surface(s).

The apparatus for each stage shown in FIG. 8 is conventional in the art and therefore not described in detail herein.

Following functionalisation, at stage 104, the treated surface(s) of the medical device will have a very high surface energy. In tested examples, total surface energies in the region of 70 Dynes/cm have been measured using the OWRK method, much higher than the typical surface energies of 25-45 Dynes/cm achievable with prior art coating methods, as determined at a 1000 frames/second measurement rate. This very high surface energy can cause the medical device to be readily contaminated, for example if touched or placed within a dirty environment. As a result, it is important to handle the medical device very carefully after functionalisation, until the device is coated with the bioactive agent. This may be in a clean room environment, vacuum or the like. During this stage and in all subsequent stages until coating, the medical device is handled preferably without any contact made with the prepared surface(s) to be coated.

Importantly, the functionalisation of the surface by the methods taught herein result in a modification of the nature of the surface energy of the surface, in a manner which the inventors have discovered is particularly beneficial to the ability of the surface to hold bioactive or other material thereto without the need for any containment material or matrix. The functionalisation leads to an increase in the polar surface energy component related to the nature of the functionalisation and to a reduction, in many cases effective elimination, of the other polar components. For instance, functionalisation by acidification leads to an increase in polar acid surface free energy and a drop or virtual elimination of polar base surface free energy; whereas functionalisation by basification leads to an increase in polar base surface free energy and a drop or virtual elimination of polar acid surface free energy.

The polar surface free energies are more reliably measured by using the Della Volpe and Siboni (DVS) scale according to the Good-van Oss theory (vOGT) using the surften calculator and by means of a contact angle measured within $\frac{1}{1000}$ of a second of impingement, using in this example the following probes:

| Liquid | $\gamma_l$ (mJ/m$^2$) | $\gamma_l^{LW}$ (mJ/m$^2$) | $\gamma_l^{AB}$ (mJ/m$^2$) | $\gamma_{l+}$ (mJ/m$^2$) | $\gamma_l^-$ (mJ/m$^2$) |
|---|---|---|---|---|---|
| Water | 72.80 | 26.25 | 46.53 | 48.50 | 11.16 |
| Glycerol | 64.00 | 35.05 | 28.55 | 27.80 | 7.33 |
| Methylene Iodide | 50.80 | 50.80 | 0.00 | 0.00 | 0.00 |
| Ethylene Glycol | 48.00 | 33.90 | 14.15 | 0.97 | 51.60 |

In a test on a stent surface treated as taught herein with citric acid functionalisation, the polar acid surface free energy as measured by this mechanism, using glycerol as the measurement droplet for contact angle measurement, rose from around 1.1 Dynes/cm to around 3.6 Dynes/cm with, importantly, a drop in the polar base component from around 0.22 Dynes/cm to zero. This resulted in a significant increase in the acid to base polar surface energy component and as a consequence a significant increase in the adhesion of a conjugate bioactive material layer posited onto the treated surface.

Figure 10:
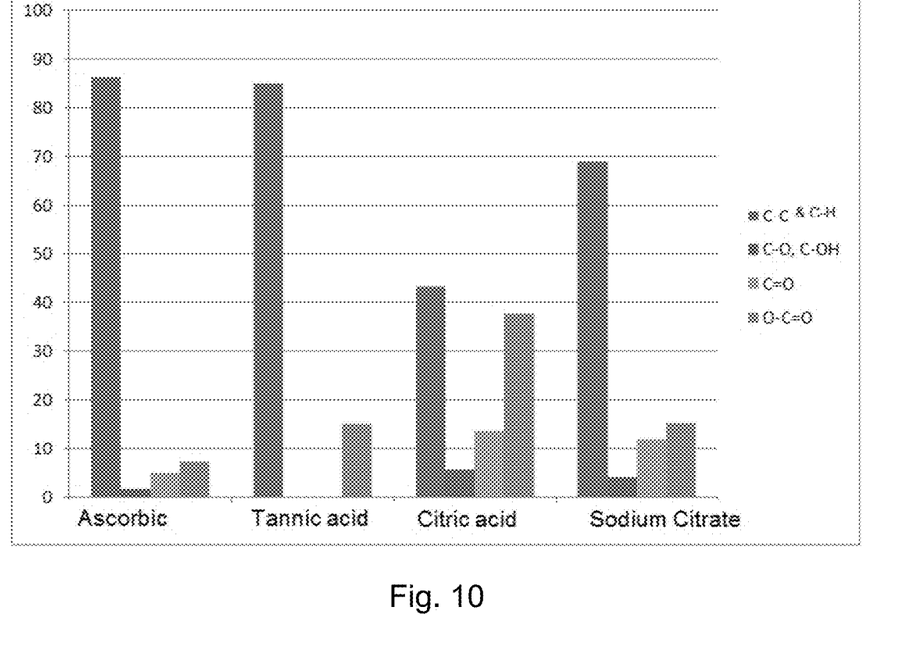
FIG. 10 is a bar graph showing the effect of surface functionalisation of a Nitinol stent with a variety of acids.

Referring now to FIG. 10, this is a bar graph showing the effects of functionalisation of an acid coated Nitinol stent by means of a variety of acids. In particular, it can be seen that this functionalisation results in a preponderance of C—C and C—H bonds in the carbon coating, and lesser components of C—O, C—OH, C=O and O—C=O. The surface functionalisation by acidification, as explained above, increases the binding qualities of the stent surface and reduces the deviation in quantity of bioactive agent, being the conjugate of the acidic base, which is held on the stent surface.

The application of acidic functional groups may be carried out in a variety of manners, including dipping, rolling or spraying acid in solution, typically ethanol or water. The inventors have discovered that using water or ethanol as the solvent, particularly with citric acid, produces consistently lower RSD values. Tests have also established that for these purposes a concentration of 1% citric acid is optimal, although concentrations from 0.1% to 10% have also been found to work. This may be applied in a plurality of spray passes, typically from around 5 to 20 passes, most preferably from around 10 to 20 passes. A greater concentration of acid or a greater number of passes can result in an excessive amount of acid molecules being deposited onto the stent surface, which is not desired, and also an increase in the RSD of the amount of drug applied to the functionalised surface.

Figure 11:
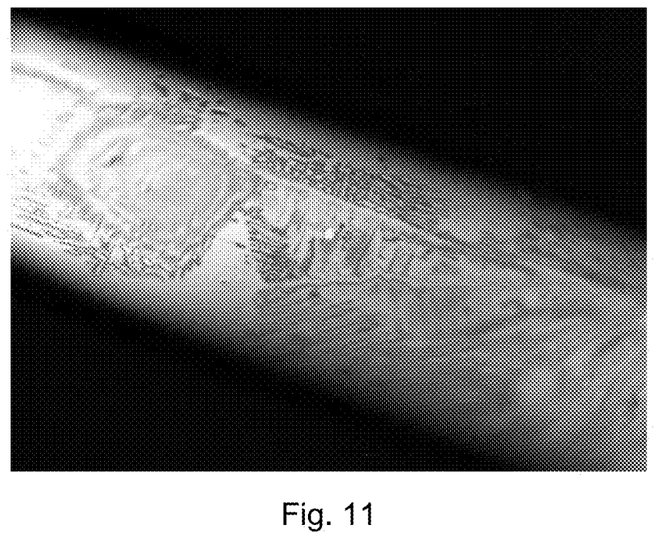
FIGS. 11 to 15 are photographs of parts of a Nitinol stent having the shown surfaces functionalised by a variety of acidic treatments.
Figure 12:
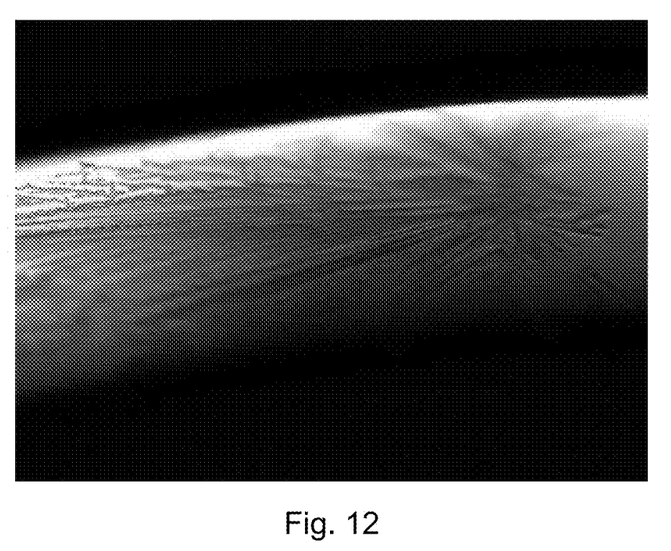

Referring to FIGS. 11 to 15, these are photographs of the functionalised surfaces of Nitinol stents under polarised light. In all cases shown in these photographs, the stents were functionalised with citric acid by spraying. The close-up photographs of FIGS. 11 and 12 show the spread of acid molecules on the surface of the stent caused by high energy spraying, the stent having been plasma cleaned. As will be apparent, the acid molecules do not cover the entirety of the treated stent surface, and it has been found that this can provide a good base for an even layer of bioactive agent, for instance paclitaxel, on the stent surfaces, with little deviation in the amount of drug across the stent surface and from one stent to another in a batch. Typically, acidification by a 1% citric acid concentration in water can provide an RSD of 2.0% or less and a base for holding a significant amount of bioactive agent, for instance more than 400 micrograms of PTX on a 40 mm long stent (of surface area of around 500 $mm^2$). Plasma cleaning of the stent, with subsequent protection of the surface prior to functionalisation of the surface, increases the receptivity of the surface to the acid (or base) functional components. In the absence of atomic cleaning, by plasma preferably, the surface may be less receptive to functionalisation, leading to discrete and separated globules or zones of acid or base components and loss of spread of these molecules across the surface.

Figure 13:
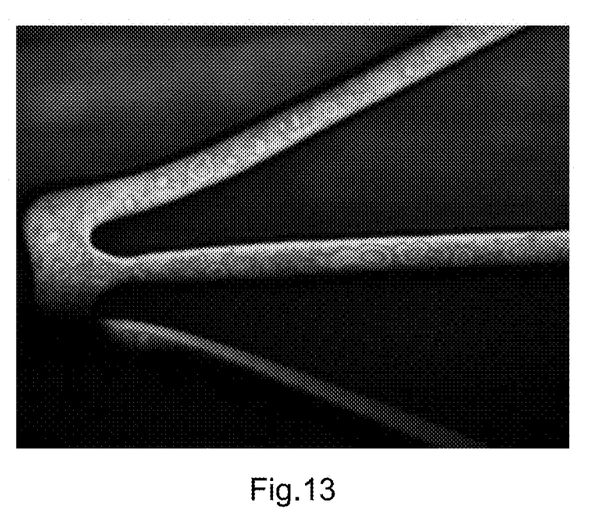
Figure 14:
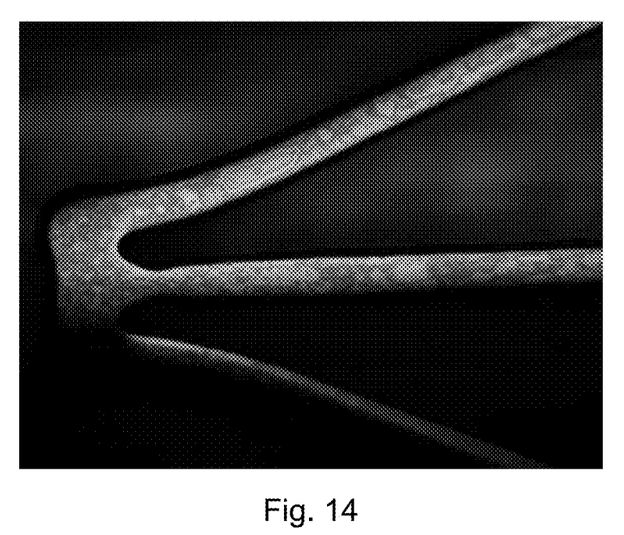
Figure 15:
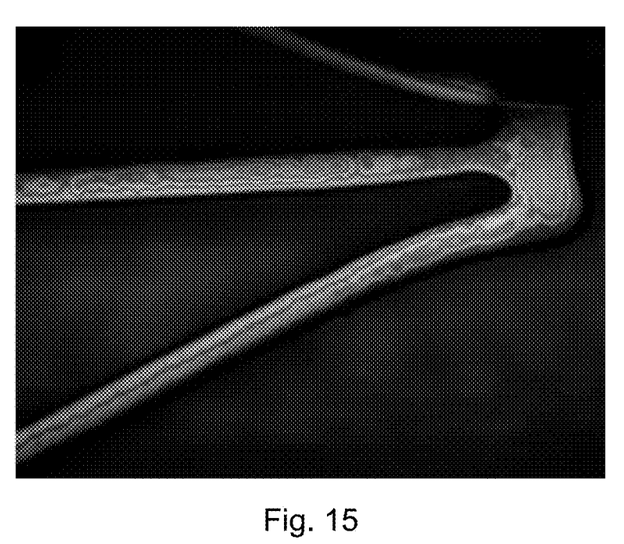

FIG. 13 shows part of a stent which has been treated with 1% citric in water sprayed onto the plasma cleaned surfaces of the stent over 10 passes. FIG. 14 shows part of a stent which has been treated with 1% citric in water sprayed onto plasma cleaned surfaces of the stent over 15 passes. Similarly, FIG. 15 shows part of a stent which has been treated with 1% citric in water sprayed onto plasma cleaned surfaces of the stent over 20 passes.

In practical tests, it has been found that for a plasma cleaned stent coated with 1% citric acid solution a greater number of passes over the stent leads to an improvement in the uniformity of drug dosage of the stents. For example, on a typical 40 mm stent previously plasma cleaned as taught herein, an average coating of paclitaxel of between 425 and 460 microgram's was achieved, with an RSD in paclitaxel coating amount ranging from about 4.5% with up to five passes of citric acid solution over the stent contact surfaces, down to around 2.0 to 2.5% with ten to fifteen passes of citric acid solution over the stent contact surfaces, down to around 1.5% with around twenty passes. This demonstrates that functionalisation of the contact surface with an acid, and similarly with a base, improves significantly the coating characteristics of stents or other medical devices.

For a stent having a surface area of around 500 $mm^2$ it has been found that the optimal amount of acid applied on the stent of around 80 to 150 micrograms, preferably 100 micrograms, in other words around 0.16 to 0.3 micrograms, preferably around 0.19 micrograms of acid per square millimetre of treated stent surface. This leads to a thickness of around 100 to 170 nanometres. The acid may be applied across the entire surface of the stent, with no gaps, but experiments have established that it is not necessary to have an even coating of acid on the stent surface. The functionalisation by spraying applies enough acidic component to the contact surface as to provide the stated benefits of enhanced drug retention and greater uniformity across the stent, particularly with multiple passes across the surfaces, and from one stent to another in a batch that prior art coating and cleaning methods.

The skilled person will appreciate that the above applies also to functionalisation with a base.

Although the method and system described above and in conjunction with coating of a stent, the same method and system can be used to coat other medical devices, such as medical balloons. In the case of medical balloons, it is generally preferred that the bioactive agent is released quickly into the patient's tissues and for this purpose an excipient, such as urea and/or urea derivatives, gallates and gallate derivatives (such as epi gallo catechin gallate), saccharides and/or saccharide derivatives, chitin and/or chitin derivatives, ascorbic acid, citric acid, sterates and/or sterate derivatives, polyvinyl pyrolidone, dicalcium phosphate dihydrate, eudragit polymers and/or eudragit polymers derivatives, cellulose and/or cellulose derivatives, PEG, poylsorbate 80, sodium lauryl sulphate, chitosan, magnesium dioxide, silicon dioxide, carbonate derivatives, plasdone, butylated hydroxyanisole, succinic acid, sodium dioctyl sulfosuccinate, precirol ATO 5, may be added to the bioactive agent. The excipient will speed up the release of the bioactive agent once the medical device is deployed within the patient, for instance by the excipient dissolving within the patient's blood plasma and providing for quick release of the bioactive agent. This can be particularly useful in treating initial reactive hyperplasia occurring as a result of angioplasty or other medical procedures. Where an excipient is used, this may be as a sublayer between the layer of bioactive material and the medical device or as a layer above the layer of bioactive material. The excipient acts to speed the release of the bioactive agent (drug for example), compared to a drug per se or a drug held in a containment or time release layer. In the case of a sublayer of excipient, the functionalisation of the surface to be coated will be matched to the nature of the excipient and the excipient matched to the bioactive agent or agents.

The bioactive material can be any of a large variety and many bioactive materials for coating medical devices are known in the art. The layer of bioactive material applied to the functionalised surfaces of the device may be of a single bioactive material or a combination of different bioactive agents, in dependence upon the desired treatment. There may also be provided other active agents in the bioactive material layer, such as excipients or other release facilitators.

The bioactive material of the coating may include at least one of: paclitaxel and/or paclitaxel derivatives, rapamycin and/or rapamycin derivatives, docetaxel and/or docetaxel derivatives, cabazitaxel and/or cabazitaxel derivatives, taxane and/or taxane derivatives, estrogen or estrogen derivatives; heparin or another thrombin inhibitor, hirudin, hirulog, argatroban, D-phenylalanyl-L-poly-L-arginyl chloromethyl ketone or another antithrombogenic agent, or mixtures thereof; urokinase, streptokinase, a tissue plasminogen activator, or another thrombolytic agent, or mixtures thereof a fibrinolytic agent; a vasospasm inhibitor; a calcium channel blocker, a nitrate, nitric oxide, a nitric oxide promoter or another vasodilator an antimicrobial agent or antibiotic; aspirin, ticlopdine or another antiplatelet agent; colchicine or another antimitotic, or another microtubule inhibitor; cytochalasin or another actin inhibitor; a remodelling inhibitor; deoxyribonucleic acid, an antisense nucleotide or another agent for molecular genetic intervention; GP IIb/IIIa, GP Ib-IX or another inhibitor or surface glycoprotein receptor; methotrexate or another antimetabolite or antiproliferative agent; an anti-cancer chemotherapeutic agent; dexamethasone, dexamethasone sodium phosphate, dexamethasone acetate or another dexamethasone derivative, or another anti-inflammatory steroid; dopamine, bromocriptine mesylate, pergolide mesylate or another dopamine agonist; 60Co (having a half-life of 5.3 years), 192Ir (73.8 days), 32P (14.3 days), 111In (68 hours), 10 90Y (64 hours), 99 mTc (6 hours) or another radio therapeutic agent; iodine containing compounds, barium-containing compounds, gold, tantalum, platinum, tungsten or another heavy metal functioning as a radiopaque agent; a peptide, a protein, an enzyme, an extracellular matrix component, a cellular component or another biologic agent; captopril, enalapril or another angiotensin converting 15 enzyme (ACE) inhibitor; ascorbic acid, alphatocopherol, superoxide dismutase, deferoxyamine, a 21-aminosteroid (lasaroid) or another free radical scavenger, iron chelator or antioxidant; angiopeptin; a 14C-, 3H-, 131I1-, 32P- or 36S-radiolabelled form or other radio labelled form of any of the foregoing; or a mixture of any of these.

The teachings herein have also been tried with tannic acid with significant benefits. Tannic acid molecules are relatively large and it has been found are particularly effective for binding bioactive agents, such as paclitaxel, to a medical device, achieving significant dosages of agent to the medical device. Tannic acid can also act as an excipient as it speeds the release of the bioactive agent once hydrolysed. Other tests has used with success: lactic acid, acetic acid, formic acid, ascorbic acid, propionic acid, phosphonic acid and phosphoric acid.

The teachings herein make it possible to attach bioactive agents to the surfaces of medical devices without having to rely on binding agents or polymer of other matrix materials as in the prior art. Binding agents are considered to be substances which enhance the adhesion of a bioactive material layer at the support surface and generally act to retard the release of the bioactive agent or agents. A polymer or other matrix performs a similar role. Binding agents and matrices act as containment mechanisms.

As has been described above, the teachings herein can be applied to a variety of medical devices including, in addition to the examples already indicated, vascular filters, vascular plugs, coils, neural vascular devices, pacemakers, prostheses, surgical tools, catheters, and so on. The bioactive agent can also be agents for inflammation reduction, for reducing vascular spasm, prosthesis acceptance, bone and tissue growth promoters, and so on All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosures in British patent application number 1600808.8, from which this application claims priority, and the abstract accompanying this application are incorporated herein by reference.

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

We claim:

1. A method of coating a medical device having a structure for implantation or disposition inside a patient, the structure including at least one surface for coating, the method including the steps of:
    functionalizing the at least one surface of the structure by subjecting the at least one surface to acidification by a carboxylic acid, to form at least one functionalized surface; and
    applying a material coating directly to the at least one functionalized surface of the medical device, the coating comprising a bioactive material to be released from the medical device, the coating being a conjugate base or including a conjugate base component of the carboxylic acid,
    wherein the functionalizing does not form a polymer matrix on the at least one surface.

2. A method according to claim 1, wherein the step of functionalizing the at least one surface causes an increase in acidic polar components at the at least one surface.

3. A method according to claim 1, wherein the coating:
    a) consists of or is principally of bioactive material;
    b) is or includes a therapeutic substance;
    c) is or includes an anti proliferative bioactive substance; or
    d) is or includes paclitaxel.

4. A method according to claim 1, wherein the coating is free of at least one of:
    a) containment elements;
    b) binding agents;
    c) time control release agents; and
    d) polymer or other matrix material.

5. A method according to claim 1, wherein the functionalized surface is substantially impervious to the material coating.

6. A method according to claim 1, wherein the entirety of the at least one surface is functionalized.

7. A method according to claim 1, wherein the step of functionalizing the at least one surface does not remove or altering oxide on the at least one surface.

8. A method according to claim 1, further including the step of atomically cleaning the at least one surface prior to functionalization, said atomic cleaning being without removal of oxide on the at least one surface.

9. A method according to claim 1, further including the step of cleaning the at least one surface with an alcohol prior to functionalization.

10. A method according to claim 1, wherein the at least one surface is functionalized by treatment for around five minutes.

11. A method according to claim 1, wherein the at least one surface is functionalized by treatment with one or more of: citric acid, acetic acid, lactic acid, alginic acid, adipic acid and conjugates and derivatives thereof.

12. A method according to claim 1, wherein the at least one functionalized surface includes a dispersal facilitator including a C—C component.

13. A method according to claim 1, wherein the medical device is or includes:
    a) a stent or balloon;
    b) a stent and wherein the structure is made of nickel titanium alloy; or
    c) a balloon and the coating includes an excipient.

14. A medical device including: a structure for implantation or disposition inside a patient, the structure including at least one surface for coating;
    wherein the at least one surface is functionalized by a carboxylic acid, so as to be a functionalized surface; and a material coating disposed directly on the at least one functionalized surface of the medical device, the coating comprising a bioactive material to be released from the medical device, the coating being a conjugate base or including a conjugate base component of the carboxylic acid, and wherein the functionalizing does not form a polymer matrix on the at least one surface.

15. A medical device according to claim 12, wherein the at least one functionalized surface has an increased acidic polar composition compared to a remainder of the structure of the medical device.

16. A medical device according to claim 12, wherein the coating:
   a) consists of or is principally of bioactive material;
   b) is or includes a therapeutic substance;
   c) is or includes an anti proliferative bioactive substance; or
   d) is or includes paclitaxel.

17. A medical device according to claim 12, wherein the coating is free of at least one of:
   a) containment elements;
   b) binding agents;
   c) time control release agents; and
   d) polymer or other matrix material.

* * * * *